US012447039B2

(12) United States Patent
Kilbey

(10) Patent No.: US 12,447,039 B2
(45) Date of Patent: Oct. 21, 2025

(54) SYSTEM AND METHOD FOR PROVIDING A RECONFIGURABLE SLING

(71) Applicant: Bryan E. Kilbey, DeFuniak Springs, FL (US)

(72) Inventor: Bryan E. Kilbey, DeFuniak Springs, FL (US)

( * ) Notice: Subject to any disclaimer, the term of this patent is extended or adjusted under 35 U.S.C. 154(b) by 304 days.

(21) Appl. No.: 17/978,333

(22) Filed: Nov. 1, 2022

(65) Prior Publication Data

US 2024/0139020 A1 May 2, 2024

(51) Int. Cl.
*A61F 5/37* (2006.01)

(52) U.S. Cl.
CPC .................................. *A61F 5/3738* (2013.01)

(58) Field of Classification Search
CPC ........ A61F 5/37; A61F 5/3723; A61F 5/3738; A61F 5/3746; A61F 5/0118; A61F 5/05858; A61F 5/05866; A61F 5/373; A61F 5/3761; A61F 5/3753; A61F 5/40
See application file for complete search history.

(56) References Cited

U.S. PATENT DOCUMENTS

2005/0010147 A1* 1/2005 Kazmierczak ........ A61F 5/3753 602/4

* cited by examiner

*Primary Examiner* — Ophelia A Hawthorne
(74) *Attorney, Agent, or Firm* — J. Wiley Horton

(57) ABSTRACT

A reconfigurable sling assembly. The sling assembly is configured to attach to a separate belt assembly worn around a user's waist. The medial portions of the sling assembly can be selectively attached to the belt assembly. The sling assembly includes a strap for adjustably securing the user's upper arm in a position adjacent to the torso. The sling has a conventional loop arrangement for encircling and securing the lower arm. However, the loop arrangement can be placed in one of two states. In a closed state, the loop arrangement secures the lower arm against the belt assembly and inhibits any significant motion of the lower arm. However, in an open state of the loop arrangement, the lower arm is released from the sling and is free to move. In the open state the upper arm is preferably still restrained.

20 Claims, 13 Drawing Sheets

SYSTEM AND METHOD FOR PROVIDING A RECONFIGURABLE SLING

BACKGROUND OF THE INVENTION

1. Field of the Invention

This invention relates to the field of medical products. More specifically, the invention comprises an arm sling that can be reconfigured between a first position in which the upper and lower arm are held in place and a second position in which the upper arm is held in place but the lower arm is free to move.

2. Description of the Related Art

Arm slings are generally used to immobilize an arm following an injury or during a surgical recovery period. A wide variety of arm slings are commercially available. These generally secure the upper and lower arm in a fixed relationship relative to the torso. Immobilization is important in some aspects of treatment and recovery. However, it is also important for the arm to be free to move outside the confines of the sling in order to perform physical therapy and other actions.

There are currently some arm slings that allow a user to switch between full immobilization and partial immobilization of the affected arm. However, the existing slings providing this capability tend to be complex. This complexity adds expense and impairs their widespread adoption. It would be preferable to provide a reconfigurable sling that is made using only inexpensive fabric panels. The present invention provides such a solution.

BRIEF SUMMARY OF THE PRESENT INVENTION

The present invention comprises a reconfigurable sling assembly. The sling assembly is configured to attach to a separate belt assembly worn around a user's waist. The medial portions of the sling assembly can be selectively attached to the belt assembly. The sling assembly includes a strap for adjustably securing the user's upper arm in a position adjacent to the torso. The sling has a conventional loop arrangement for encircling and securing the lower arm. However, the loop arrangement can be placed in one of two states. In a closed state, the loop arrangement secures the lower arm against the belt assembly and inhibits any significant motion of the lower arm. However, in an open state of the loop arrangement, the lower arm is released from the sling and is free to move. In the open state the upper arm is preferably still restrained.

REFERENCE NUMERALS IN THE DRAWINGS

Figure 1:
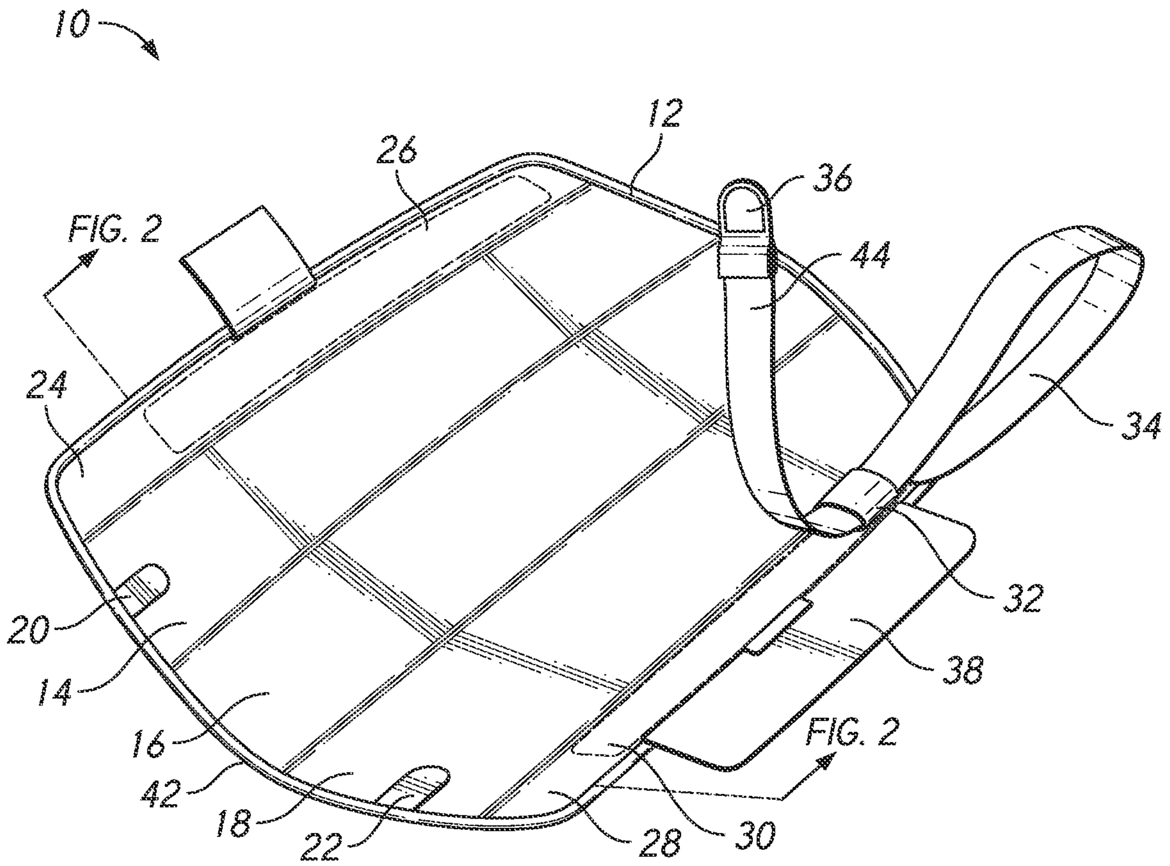
FIG. 1 is a perspective view, showing the inventive reconfigurable sling

10 reconfigurable sling assembly
12 body
14 distal panel
16 central panel
18 proximal panel
20 tab
22 tab
24 distal upper pocket
26 distal stay
28 proximal upper pocket
30 proximal stay
32 securing loop
34 upper arm loop
36 hook panel
38 superior securement flap
40 folded flap
42 anterior edge
44 strap
48 butterfly
50 lateral securement strap
52 posterior extension
54 anterior extension
56 abduction pillow
58 anterior flap
60 posterior flap
62 slot
64 belt
66 hook panel
68 free end
70 thumb pocket
72 finger pocket
74 abduction pillow foam insert 76 lateral surface
78 medial surface
80 central channel
82 anterior channel
84 posterior channel
86 anterior surface
88 posterior surface
90 sling and belt assembly
92 superior surface
94 superior securing tab
96 belt assembly
98 user
100 affected arm
102 lower arm
104 fixed end
106 target strip
108 free hand

DETAILED DESCRIPTION OF THE INVENTION

Figure 5:
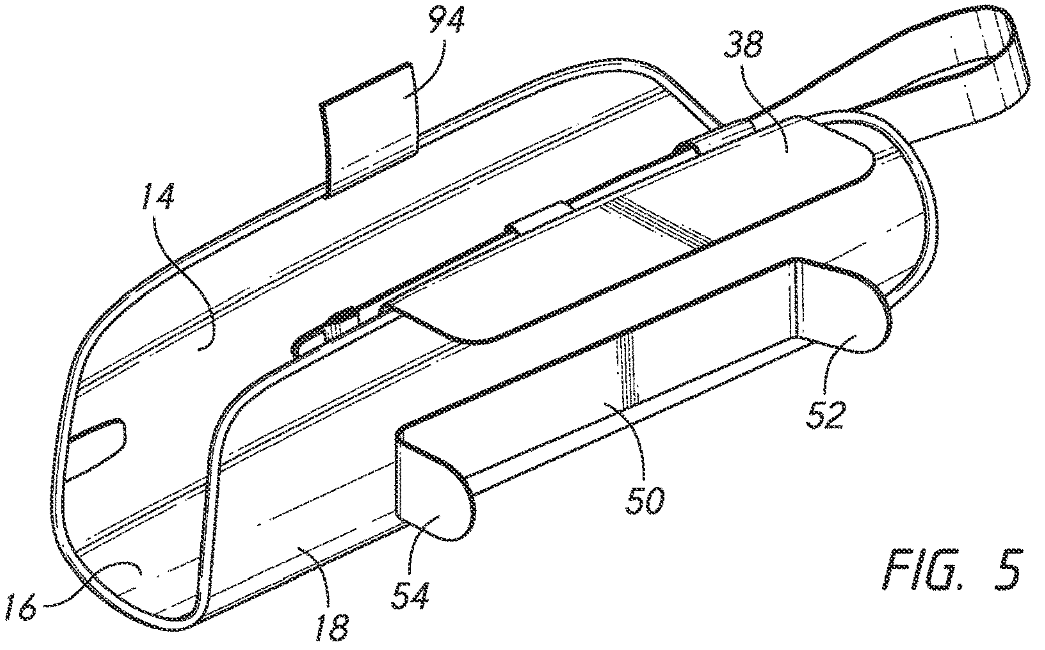
FIG. 5 is a perspective view, showing some of the attachment features located on the inventive sling.

The present invention has two major assemblies—a reconfigurable sling assembly and a belt assembly. FIG. 1 shows reconfigurable assembly 10. Central panel 16 joins proximal panel 18 to distal panel 14. The three panels 14,16,18 are configured to bend into a U-channel or loop arrangement around the lower arm (The bent or looped configuration is shown in FIG. 5). FIG. 1 shows the panels in a flattened state. In the example shown the three panels 14,16, 18 are made as one unitary piece. However, they can also be made as three distinct panels that are joined together.

The invention is not limited to any particular manufacturing method. However, the embodiment shown in FIG. 1 is made by stitching together fabric flat patterns. Two or more layers are stacked and an edge band is added around the perimeter. Additional seams are added to create a hollow distal upper pocket 24 and a hollow proximal upper pocket 28. Distal upper pocket 24 contains a slidable distal stay 26 and proximal upper pocket 28 contains a slidable proximal stay 30.

Figure 2:
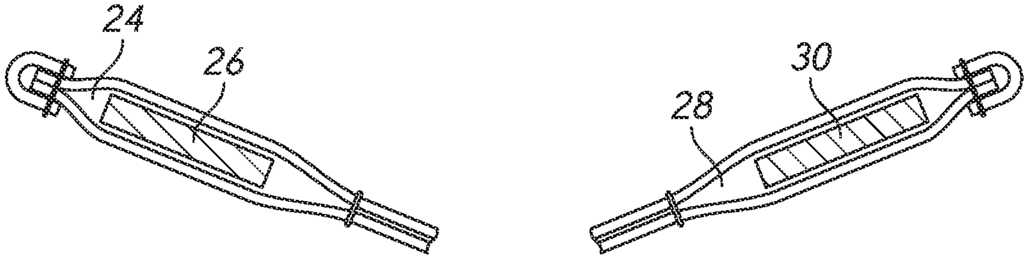
FIG. 2 is a sectional elevation view, showing some movable stays that are used to stiffen the superior edges of the sling.

FIG. 2 provides a partial section view through the two pockets 24, 28. The two stays 26, 30 rest loosely within the pockets. They serve to stiffen the superior edges of the distal panel and proximal panel. The stays may be made of any suitable material—such as plastic or aluminum.

Returning to FIG. 1, the side of the panels 14,18 facing the viewer in FIG. 1 are covered in hook-compatible material (meaning a material to which a VELCRO® hook-and-loop material hook panel will adhere). While this hook-compatible material can be VELCRO® hook-and-loop material loop, it is preferable to use a smoother and more comfortable material (since it will contact the user's lower arm). As those skilled in the art will know, many smooth fabrics can be brushed to create a small nap that makes the material hook-compatible.

Figure 3:
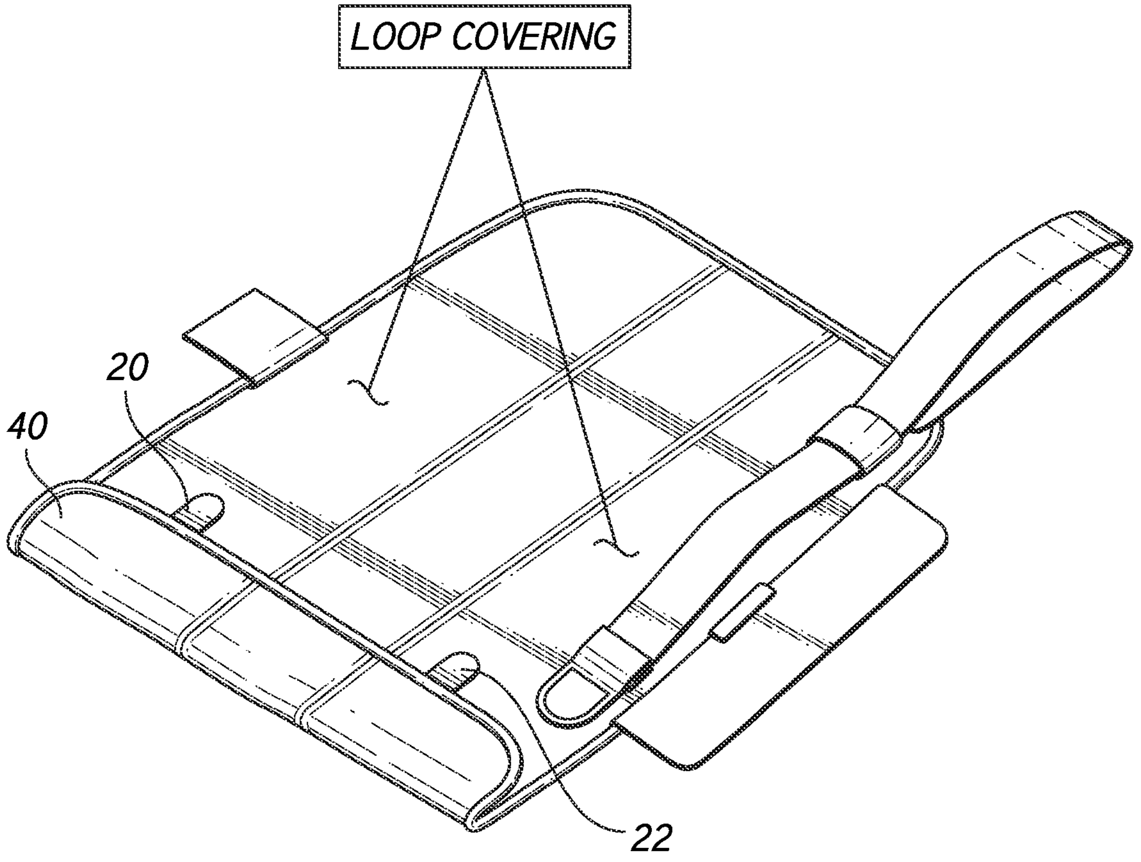
FIG. 3 is a perspective view, showing the use of a folded flap to shorten the length of the sling.

Tab 20 is attached to the anterior edge 42 of distal panel 14, while tab 22 is attached to the anterior edge of proximal panel 18. These tabs are used to optionally shorten the length of the sling. In order to shorten the sling, the user peels up tabs 20 and 22 and folds the anterior edge of the sling back on itself. The user then presses the tabs 20,22 back against the panels 14,18 to adhere the tabs in a new position. FIG. 3 shows the result. The tabs 20,22 hold the sling in the folded state. The sling can then be formed into a U or loop with a shorter overall length. Returning to FIG. 1, the user wishing to shorten the sling will also urge the stays 26, 30 in the posterior direction within their respective pockets before executing the fold along the anterior edge.

FIG. 1 also illustrates superior securement flap 38. This flap preferably extends medially from the edge of proximal panel 18. Flap 38 includes a hook panel on the side facing away from the viewer in FIG. 1. The surface of flap 38 facing toward the viewer in FIG. 1 is preferably covered with hook-compatible material.

Securing loop 32 is affixed to proximal panel 18. Strap 44 has a fixed end and a free end. The fixed end is secured to proximal panel 18. The free end is formed into upper arm loop 34 and then passed back through securing loop 32 as shown. Hook panel 36 is provided on the free end of strap 44. The free end of strap 44 is pulled in the anterior direction in order to adjust the size of upper arm loop 34. Once the desired size is achieved, hook panel 36 is pressed against the hook-compatible surface on proximal panel 18.

Figure 4:
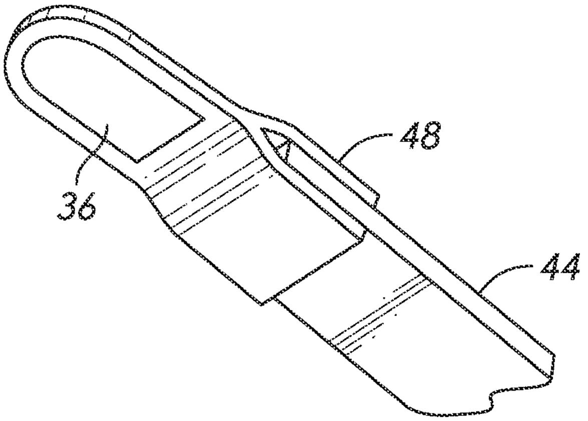
FIG. 4 is a detailed perspective view, showing the placement of a hook panel on the end of a strap.

FIG. 4 shows additional details regarding hook panel 36. In this example strap 44 is made of a material that can be cut to a desired length. Hook panel 36 is provided on a butterfly 48. Butterfly 48 contains two inward-facing hook panels that will adhere to the two surfaces of strap 44 when the butterfly is placed over the end of the strap and pressed inward. The user customarily cuts strap 44 to a desired length and then attaches butterfly 48 to the cut end.

FIG. 5 shows the sling assembly folded into the shape it will customarily assume in use. The reader will note how central panel 16 joins proximal panel 18 to distal panel 14. The assembly shown is configured for use on a user's right arm. Proximal panel 18 will lie closest to the user's torso when the sling is in use, while distal panel 14 will lie further away. Superior securement flap 38 extends medially (toward the user's torso) from the superior edge of proximal panel 18. This flap 38 is used to secure the sling assembly to the belt assembly—as will be explained subsequently.

An additional component is preferably also used to secure the sling assembly to the belt assembly. Lateral securement strap 50 is affixed to the medial side of proximal panel 18 as shown. Posterior extension 52 and anterior extension 54 are optionally provided. The medial-facing side of lateral securement strap 50 is provided with a hook panel. The anterior-facing side of posterior extension 52 and the posterior-facing side of anterior extension 54 are also provided with hook panels. Superior securing tab 94 is provided on the superior portion of distal panel 14. This tab 94 is used to close the U or loop of the sling and thereby secure the sling to the user's lower arm.

Figure 6:
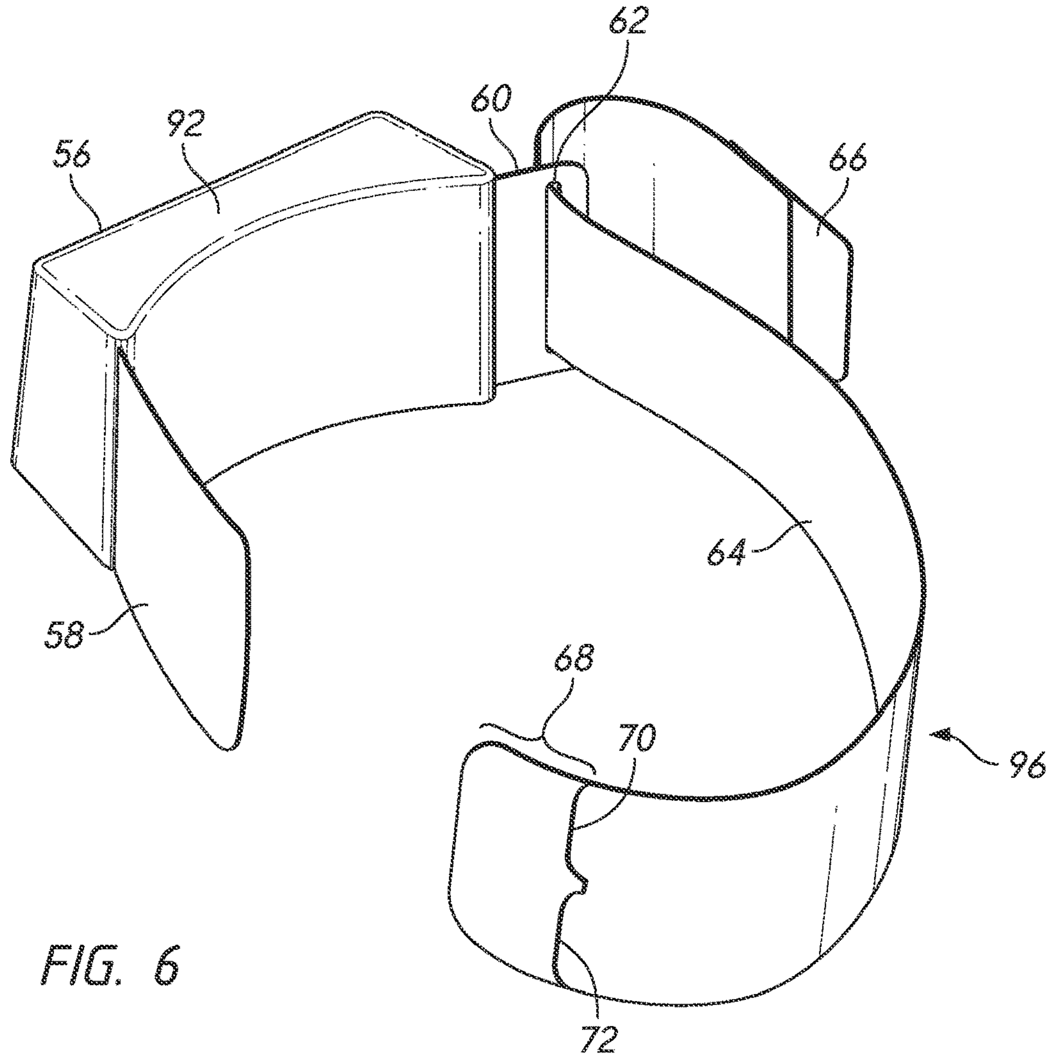
FIG. 6 is a perspective view, showing a belt assembly.

FIG. 6 shows belt assembly 96. Belt 64 is designed to encircle the user's waist and hold abduction pillow 56 on the user's lateral side. Abduction pillow 56 in this example has a posterior flap 60, which includes a slot 62 sized to allow belt 64 to pass through. The belt is passed through slot 62. The inward and outward-facing surfaces of the belt in this example are covered in hook-compatible material. Hook panel 66 is adhered to the free end of the belt with an additional portion of the hook panel 66 extending past the free end of the belt. The overall length of the belt can be adjusted by pulling the looped portion through slot 62 and adhering hook panel 66 back to the outward-facing side of belt 64 once the desired length is set.

Anterior flap 58 is affixed to the anterior side of abduction pillow 56. Free end 68 of the belt has an additional hook panel facing away from the viewer in FIG. 6. Anterior flap 58 is covered in hook-compatible material. The user secures the front portion of the belt by pressing free end 68 against the hook-compatible material on anterior flap 58. Thumb pocket 70 and finger pocket 72 are preferably provided on free end 68. These allow the user to easily manipulate the position of free end 68 by placing the thumb and fingers of one hand in pockets 70,72.

Figure 12:
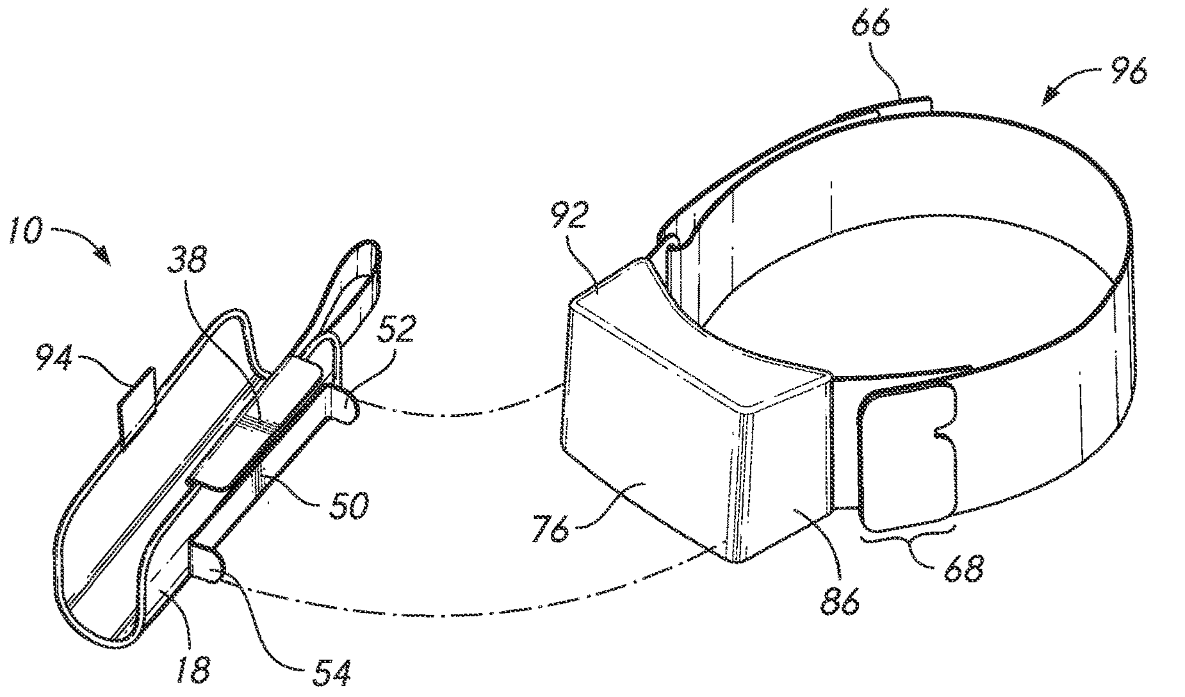
FIG. 12 is an exploded perspective view, showing a reconfigurable sling and a belt assembly in a disassembled state.

FIG. 12 shows the belt assembly in a closed state—as it will be when secured around the user's torso. Abduction pillow 56 is placed on the user's lateral side—proximate the arm that is to be placed in the sling (the "affected arm"). FIG. 12 also shows reconfigurable sling assembly 10. The dashed lines indicate approximately how the sling is to be affixed to abduction pillow 56. The downward facing side of superior securement flap 38 includes a hook panel. This hook panel is engaged with hook-compatible material on superior surface 92 of the abduction pillow. A hook panel on lateral securement strap 50 is engaged with hook-compatible material on lateral surface 76. A hook panel on anterior extension 54 is engaged with hook-compatible material on anterior surface 86. Finally, a hook panel on posterior extension 52 is engaged with hook-compatible material on a posterior surface of the abduction pillow. Preferably using these multiple points of attachment, proximal panel 18 is secured firmly to the abduction pillow.

Figure 13:
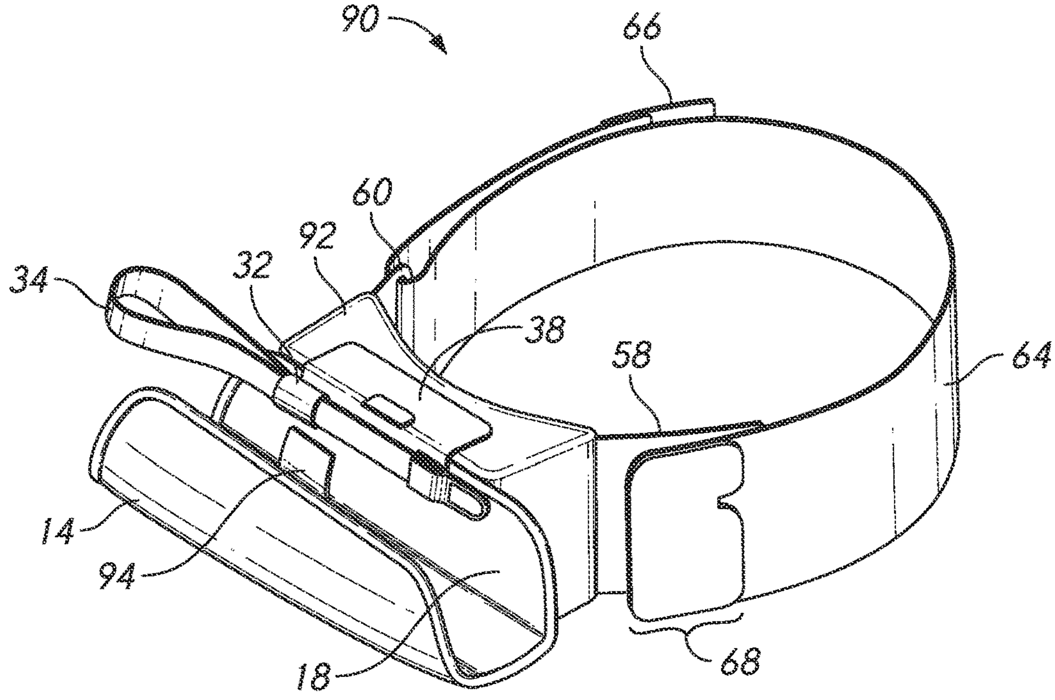
FIG. 13 is a perspective view, showing a reconfigurable sling and a belt assembly in an assembled state.

FIG. 13 shows the same configuration after the reconfigurable sling is attached to the abduction pillow. The sling is held securely against the abduction pillow. In this example, the upward facing surface of superior securement flap 38 is covered in hook-compatible material. Superior securing tab 94 is provided with a hook panel (facing away from the viewer in the vantage point of FIG. 13). The user can close the loop of the sling by pulling superior securing tab 94 over the top and pressing it against superior securement flap 38. The user can also press the superior securing tab 94 against other hook-compatible surfaces—such as surfaces on the superior surface 92 of the abduction pillow or the proximal panel 18.

In looking at FIG. 12, the reader will appreciate that the shape of the abduction pillow determines the position of the user's lower arm—and by implication the position of the shoulder joint while the affected arm is in the sling. The shape is therefore significant. The abduction pillow in this example is made by covering a foam insert with sewn fabric. FIGS. 7-11 illustrate a preferred embodiment of the foam insert.

Figure 7:
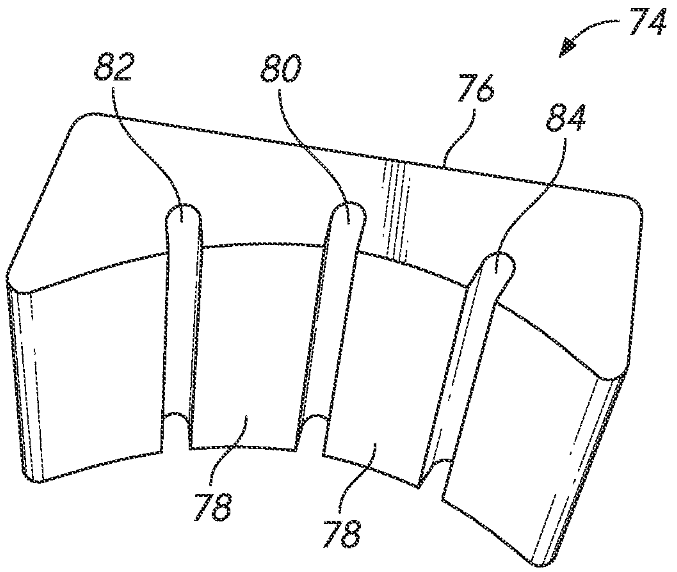
FIG. 7 is a perspective view, showing a foam insert used in an abduction pillow.

FIG. 7 shows a perspective view of abduction pillow foam insert 74 with medial surface 78—the side facing the user's lateral torso—in view. Lateral surface 76 is facing away from the viewer. The reader will note how medial surface 78 curves to follow the shape of the user's lateral torso. This introduces a challenge, however, in that the curvature of the lateral torso varies greatly from individual to individual. In order to account for this variation, medial surface 78 opens into anterior channel 82, central channel 80, and posterior channel 84.

Figure 8:
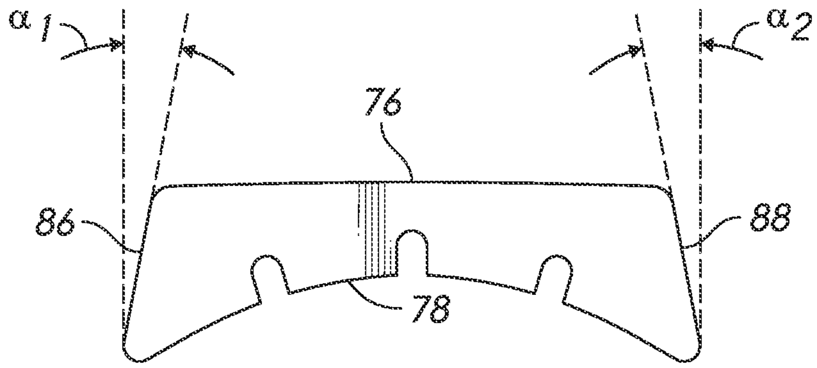
FIG. 8 is a plan view, showing the foam insert used in the abduction pillow.

FIG. 8 provides a top view of the pillow. Medial surface 78 faces the user. Lateral surface 76 faces away from the user. Anterior surface 86 faces forward and posterior surface 88 faces rearward (This is true for a right-hand configuration. The pillow can be used for a left-hand configuration, in which case anterior and posterior will be reversed). Anterior surface 86 is not perpendicular to lateral surface 76. Rather, it is angled (indicated as $\propto_1$). Posterior surface 88 is slanted in the opposite direction (indicated as $\propto_2$). The sloping anterior and posterior surfaces make it easier to affix anterior extension 54 and posterior extension 52 (see FIG. 5). The angle provided is preferably between 5 and 20 degrees, inclusive.

Figure 11:
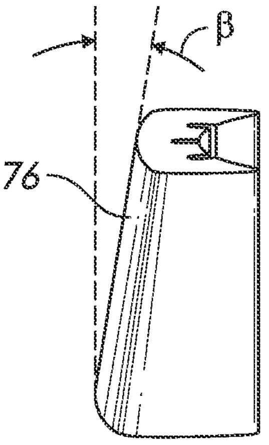
FIG. 11 is a perspective view, showing the abduction pillow.

FIG. 11 shows a view from the anterior side of the abduction pillow (looking toward the rear). Lateral surface 76 is provided with an angular offset as shown. The surface is offset from the vertical an angle β. This angle rotates the sling in order to give the shoulder joint a desired abduction angle. The angle provided is preferably between 5 and 30 degrees, inclusive.

Figure 9:
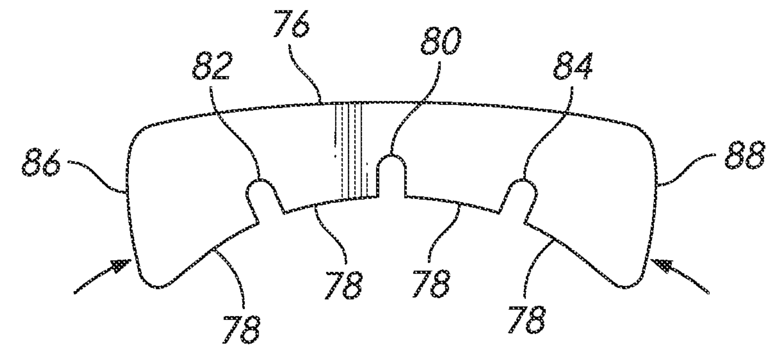
FIG. 9 is a plan view, showing the foam insert used in the abduction pillow.
Figure 10:
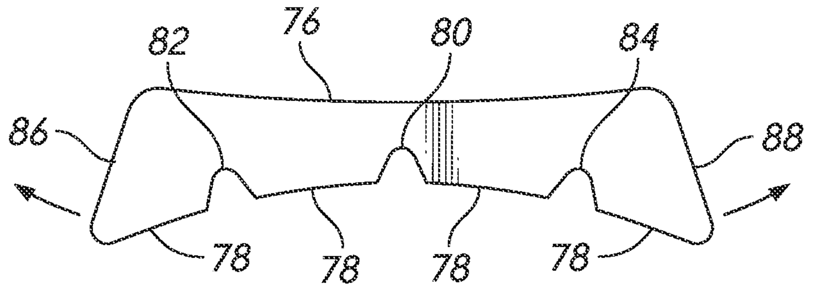
FIG. 10 is a plan view, showing the foam insert used in the abduction pillow.

FIGS. 9 and 10 illustrate the operation of the three channels 80,82,84. FIG. 9 represents the situation of an individual with a small torso. When the belt assembly is tightened the anterior and posterior side 86,88 of the abduction pillow will be squeezed toward each other as shown by the arrows. Channels 80,82,84 collapse in order to allow the foam insert to assume the compressed shape without pulling lateral surface 76 significantly out of its normal planar state (It is preferable to retain lateral surface 76 in a planar state so that the sling assembly can be more easily attached to it).

FIG. 10 shows the opposite situation. In this example the belt assembly has been passed around the torso of a very large user. The anterior and posterior sides 86,88 of the abduction pillow have been urged apart as indicated by the arrows. Channels 80,82,84 have spread open in order to allow medial surface 78 to expand without significantly deforming lateral surface 76.

Figure 14:
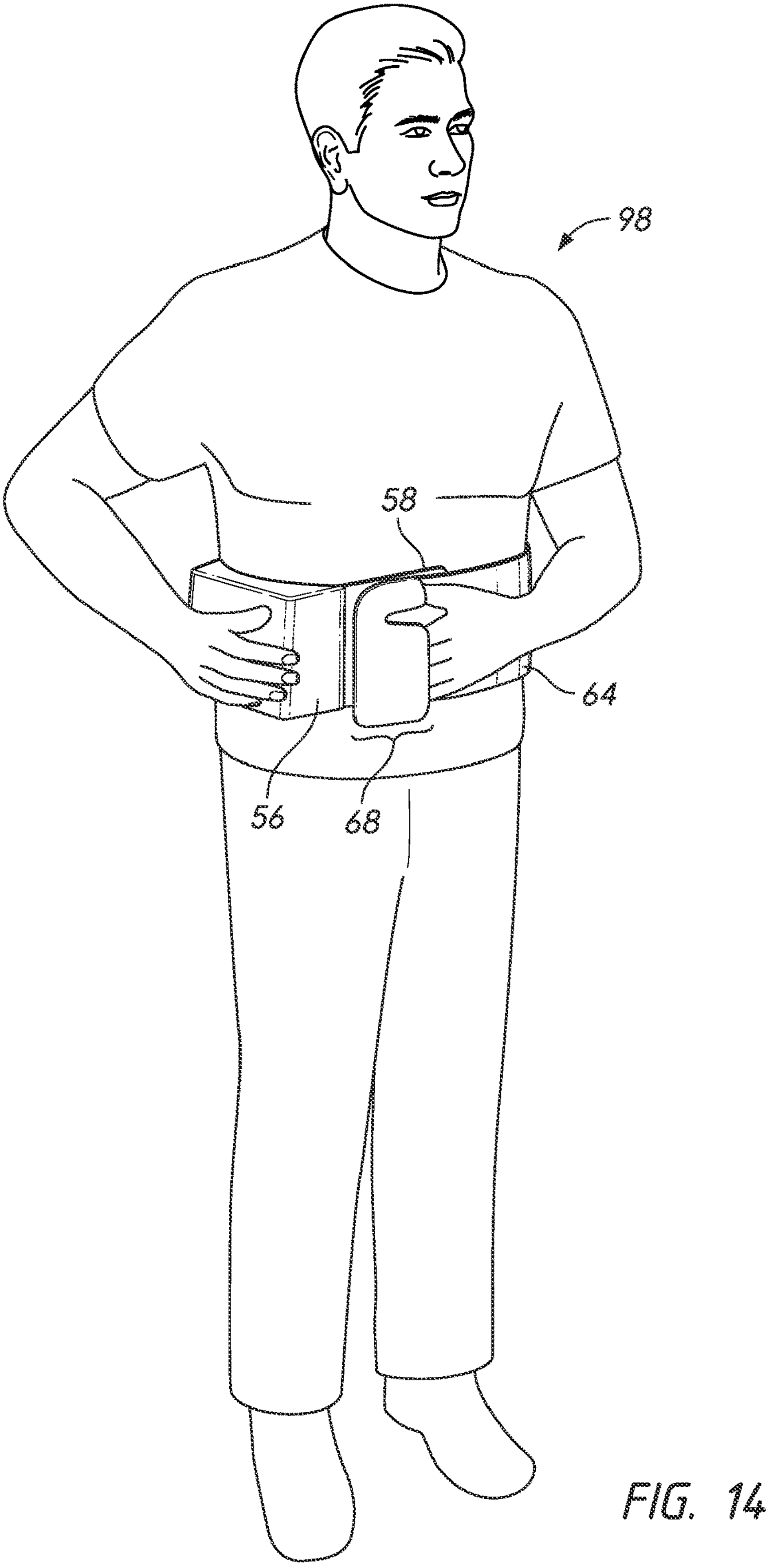
FIG. 14 is a perspective view, showing a user donning a belt assembly.

In many cases the entire assembly of FIG. 13 is supplied to the surgeon and patient in an assembled state. The assembly is then placed on the patient immediately after surgery. The ease of partial disassembly and reassembly for a patient using the available non-surgical hand is then a significant benefit as physical therapy progresses and the patient gains an increasing range of motion for the surgical arm, FIGS. 14-21 illustrate an optional progressive donning process that may be used for the inventive sling. This progressive donning process illustrates the flexible nature of the inventive sling—but does not represent the typical method of installation. FIG. 14 shows user 78 donning the belt assembly. Abduction pillow 56 has been placed on the lateral side of the torso—proximate the affected arm. The user holds the abduction pillow in place while using the other hand to press free end 68 of the belt against anterior flap 58. The hook panel on the inward-facing side of the belt's free end engages the hook-compatible material on anterior flap 58. Belt 64 is preferably made of elastic material so that it grips the user and retains the abduction pillow in place when released.

Figure 15:
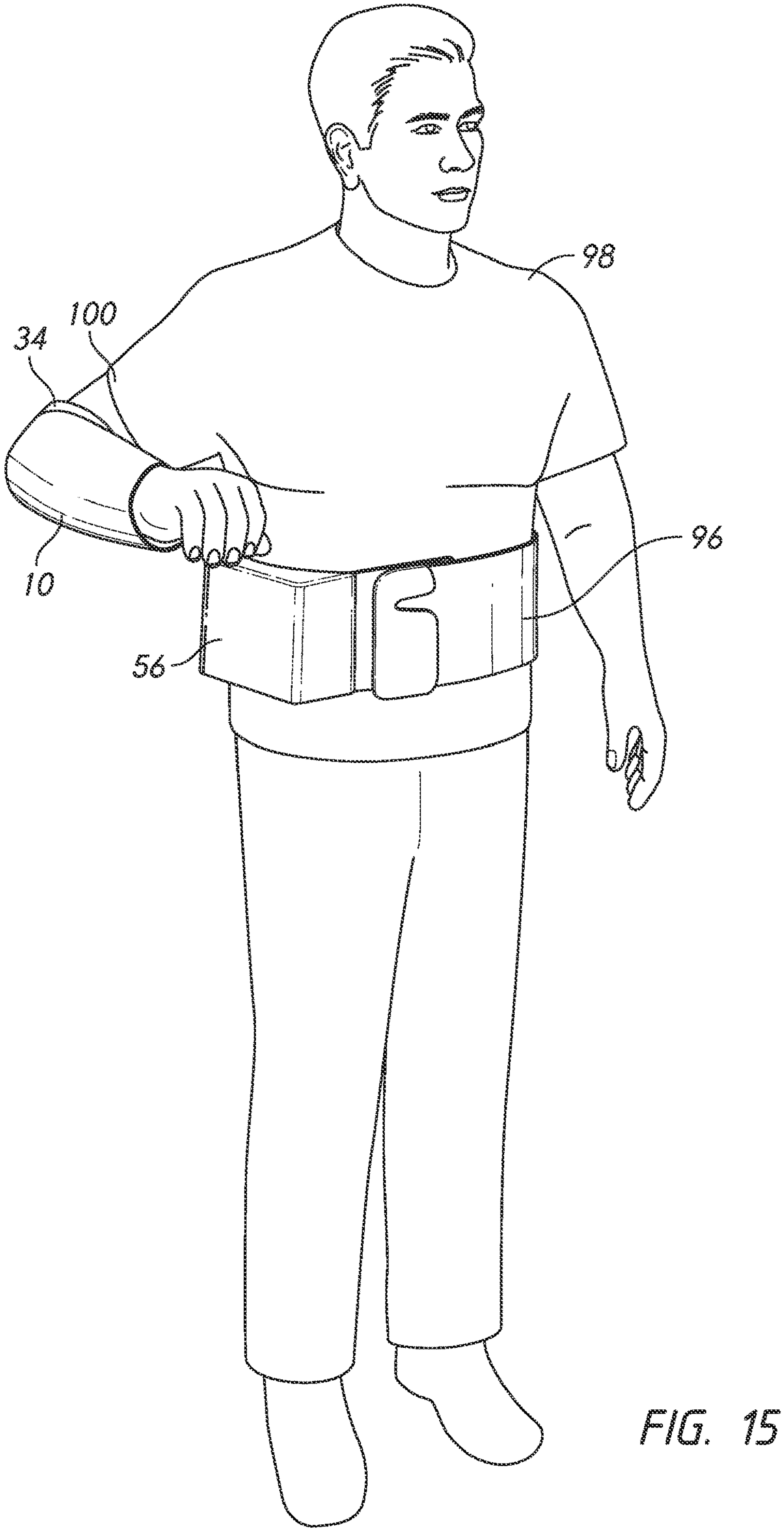
FIG. 15 is a perspective view, showing a user wearing a belt assembly and a reconfigurable sling.
Figure 16:
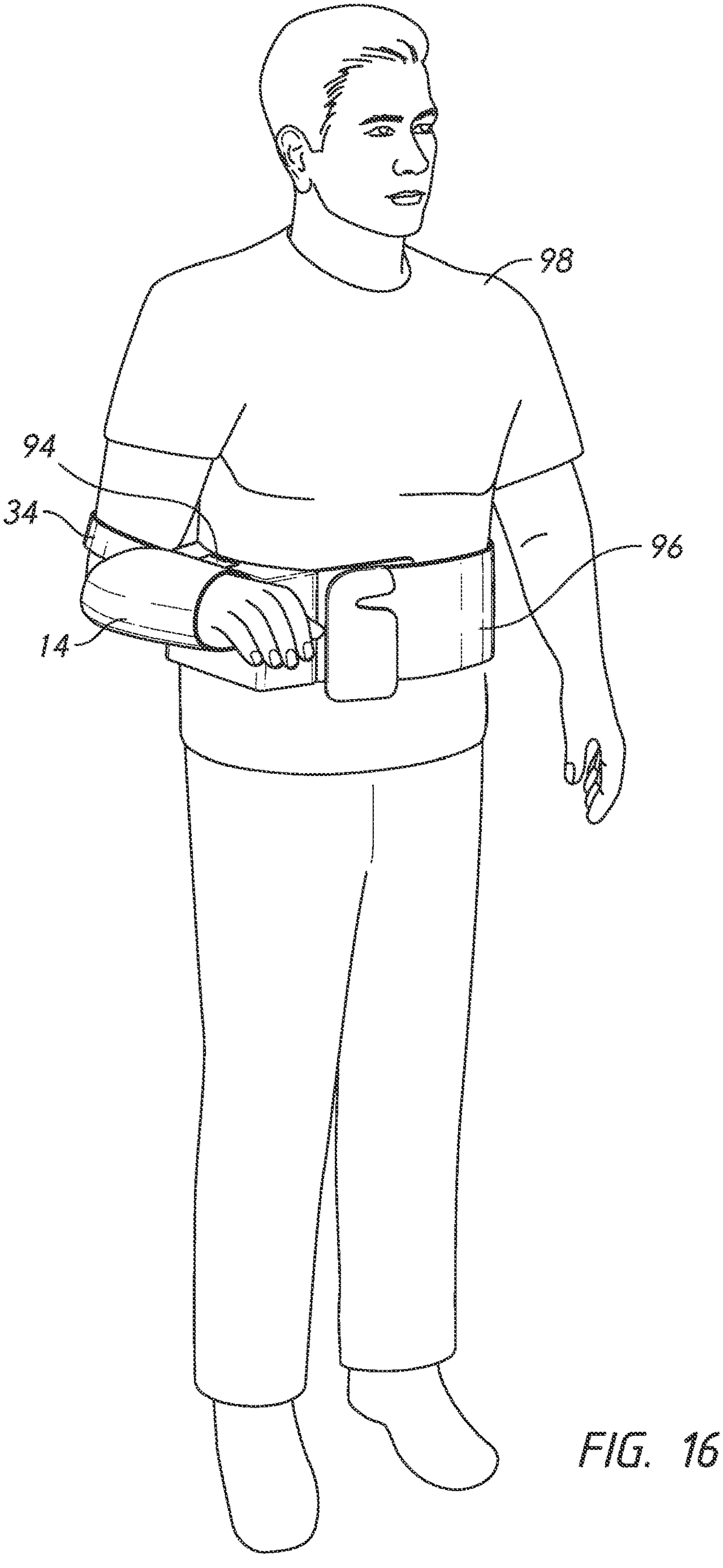
FIG. 16 is a perspective view, showing a user with a reconfigurable sling attached to a belt assembly.

FIG. 15 shows one method of assembling the sling. In this case the upper portion of affected arm 100 has been passed through upper arm loop 34 and the lower arm has been encircled by reconfigurable sling 10. The reconfigurable sling is secured on the lower arm by engaging superior securing tab 94 to superior securement flap 38 (see FIG. 5). The user—or a healthcare practitioner—then moves the shoulder in adduction so that the sling moves inward against abduction pillow 56. This is shown in FIG. 16. The sling assembly is then secured to the belt assembly as explained with respect to FIGS. 12 and 13. In FIG. 15, the end of the sling is shown stopping proximate the user's wrist. The location is dependent on whether a fold is used to shorten the sling (see FIG. 3). If no fold is used it is typical for the sling to extend to the base of the patient's little finger.

FIG. 16 shows how the upper arm is held by upper arm loop 34. Distal panel 14 is pulled up and over the top of the lower arm and superior securing tab 94 is engaged to retain the loop of the sling in the closed position.

Figure 17:
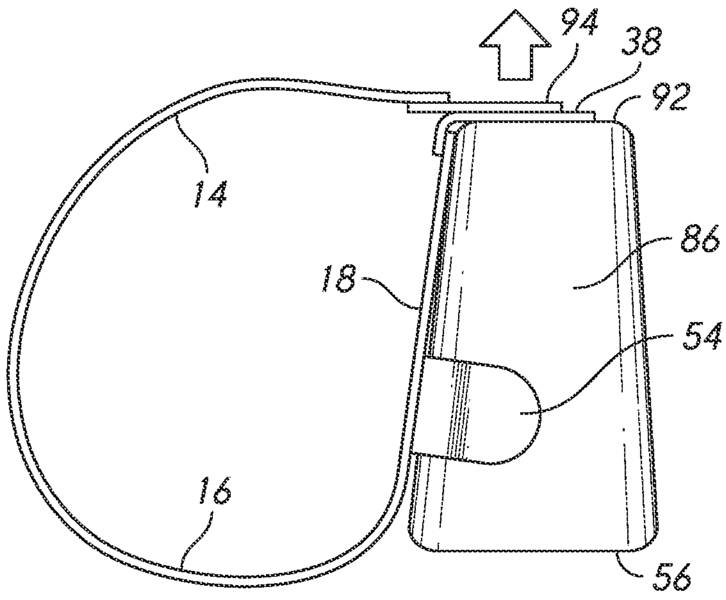
FIG. 17 is an elevation view, showing the reconfigurable sling in a closed state.
Figure 18:
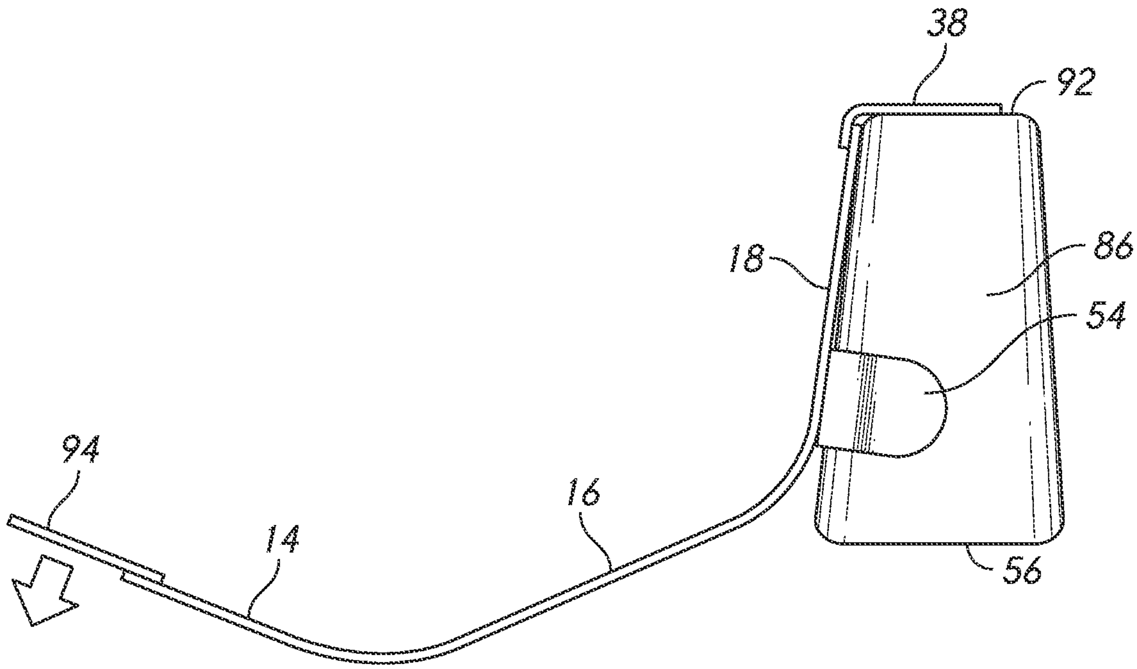
FIG. 18 is an elevation view, showing the reconfigurable sling in an open state.

FIGS. 17 and 18 provide more detail as to the engagement and disengagement of superior securing tab 94. FIG. 17 shows the loop of the sling in a closed state. Superior securing tab 94 is secured to the upper surface of superior securement flap 38. The downward-facing surface of superior securement flap 38 is engaged to superior surface 92 of the abduction pillow. Proximal panel 18, central panel 16, and distal panel 14 are thereby formed into a loop around the lower arm and retained there.

To open the loop, superior securing tab 94 is lifted upward—as indicated by the arrow in FIG. 17. The superior securing tab is pulled up and away to open the loop—as shown in FIG. 18. Still looking at FIG. 18, the reader will note that proximal panel 18 stays in position proximate abduction pillow 56 even when the sling is open. The engagement of anterior extension 54 and posterior extension 52 helps to keep the proximate panel in place.

Figure 19:
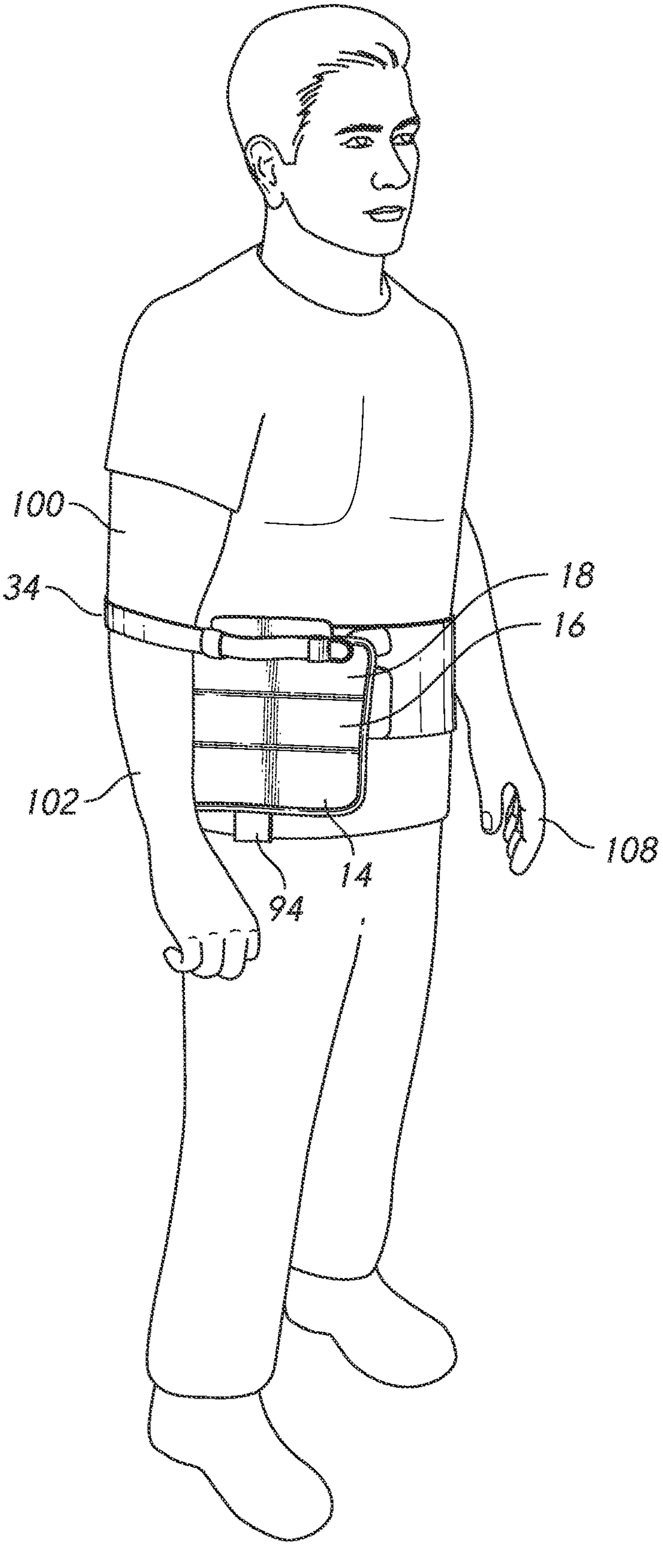
FIG. 19 is a perspective view, showing a user wearing the inventive sling in an open state.

FIG. 19 shows the inventive reconfigurable sling in an open state. Lower arm 102 has been released by opening the loop of the sling. However, upper arm loop 34 remains around the affected arm 100. Superior securing tab 94 lies flat against the user' side. The user is thus free to move the lower arm in order to perform arm circles and various other helpful rehabilitative exercises. However, the presence of upper arm loop 34 continues to prevent larger motions of the shoulder joint by holding the upper arm in position.

Figure 20:
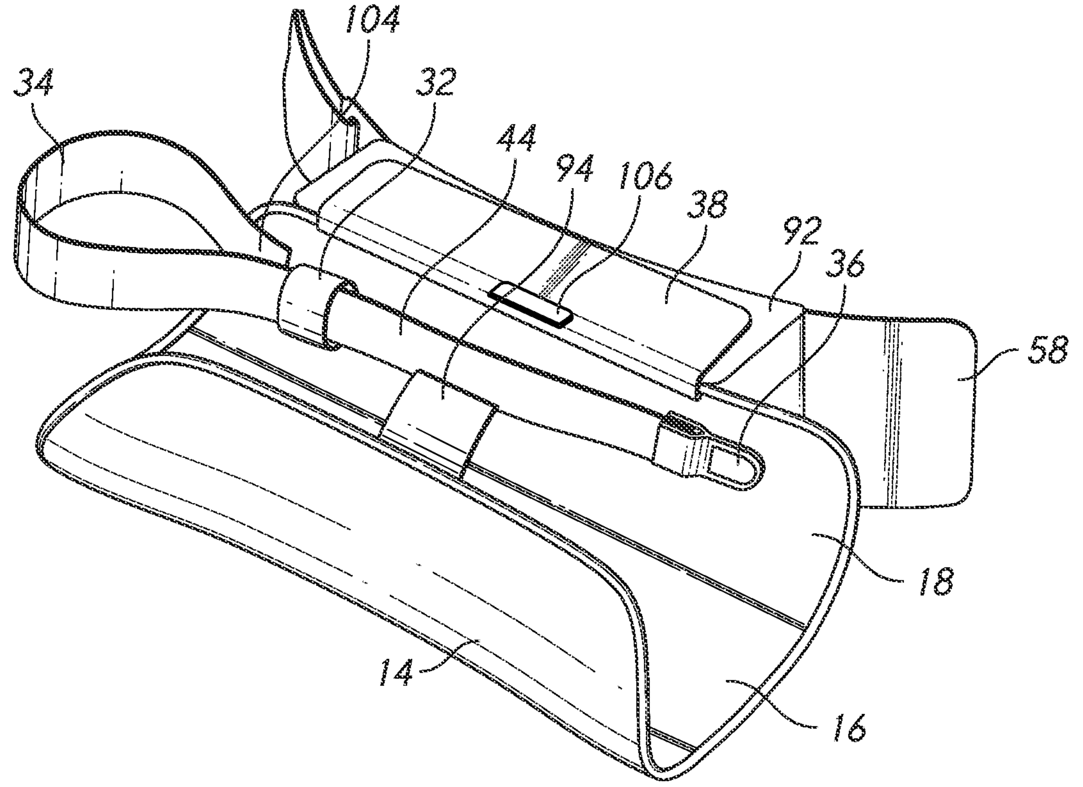
FIG. 20 is a perspective view, showing the reconfigurable sling in an open state.

The user can easily close the loop of the sling without help from another person. To do this, the user bends the elbow and raises lower arm 102 until it rests in the normal sling position. The user then grasps superior securing tab 94 with free hand 108 and raises the distal side of the sling. FIG. 20 shows the panels 14,16,18 being reformed into a loop as tab 94 is raised and pulled toward the abduction pillow (The arm is omitted in FIG. 20 for visual clarity).

Figure 21:
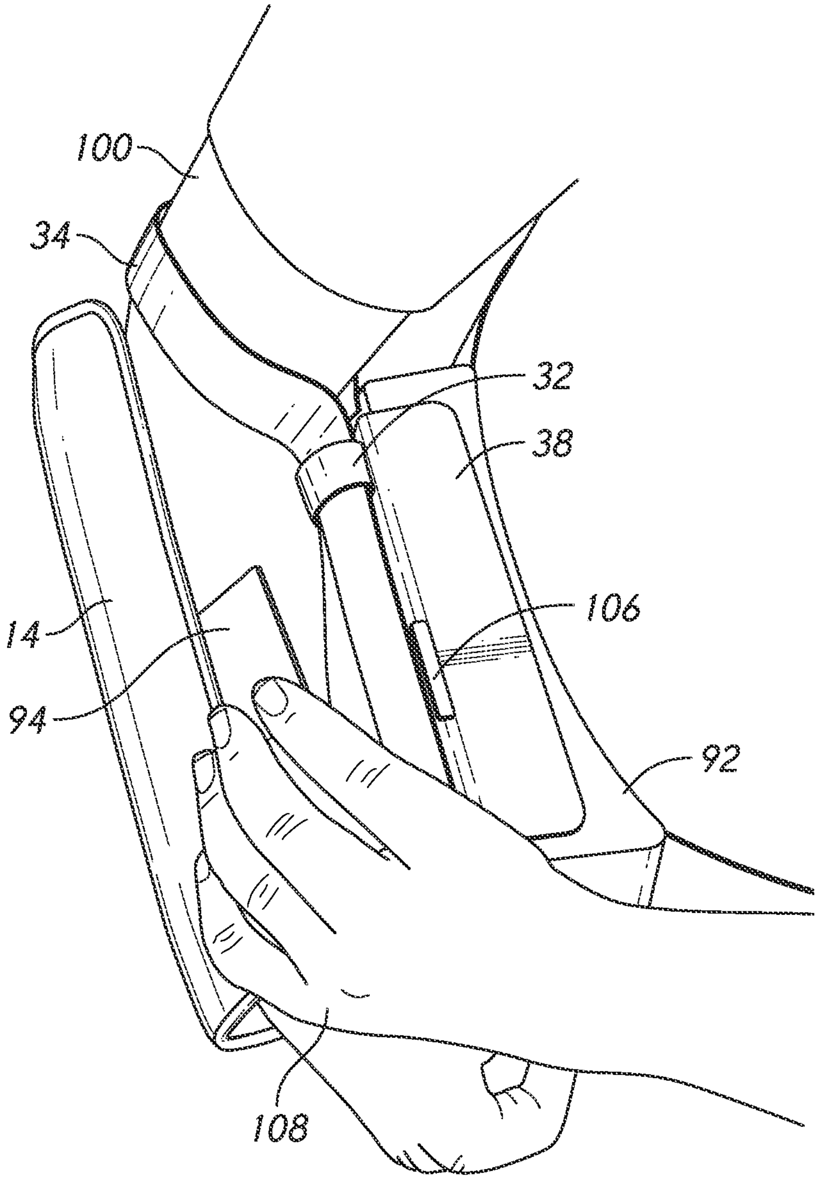
FIG. 21 is a perspective view, showing how s user can employ a free hand to open or close the inventive sling.

FIG. 21 shows the assembly with the arm included. Free hand 108 pulls superior securing tab 94 up and over to press it against superior securement strap 38—thereby closing the sling. Target strip 106 is a brightly-colored fabric piece in this example. It aids the user in achieving the correct closed position for tab 94.

It is of course unnecessary for panel 14 to close completely over the user's forearm. In some embodiments superior securing tab 94 is made much longer so that it attaches to superior securement strap 38 while the upper portion of the sling remains open.

Returning to FIG. 19, an alternate method of donning the inventive sling will be explained. The process can start with the position shown. The belt assembly has been placed and the reconfigurable sling has been mounted on the abduction pillow. The user then passes the arm through upper arm loop 34 as shown. The user then closes the loop of the sling to position the lower arm (as in FIG. 21).

FIG. 20 provides a good illustration of how the sling relates to the abduction pillow. FIG. 20 is also a good illustration of how the upper arm is easily and comfortably secured using the upper arm loop adjustment system. In this example, fixed end 104 of the upper arm loop is stitched to proximal panel 18 in the position shown. The loop is then formed and the free end of strap 44 is passed through securing loop 32. The size of the upper arm loop 34 is then adjusted by moving hook panel 36 to the right or left (in terms of the view) before pressing it against the hook-compatible material on proximal panel 18.

Many other options can be provided for the inventive sling. These include, without limitation:

1. Making the three panels 14,16,18 of one piece of material;
2. Making the three panels 14,16,18 of different types of material. As an example, central web 16 does not necessarily need hook-compatibility and may therefore be made of a highly porous material to promote air flow around the lower arm;
3. The restrain for the upper arm can assume a form other than a strap formed into a loop;
4. The hook panels and loop panels recited in the specification can be reversed;
5. The assemblies can be made in a right or left handed configuration; and
6. Omitting the abduction pillow from the belt assembly—with the sling assembly attaching to the belt itself or another component of the belt assembly.

Although the preceding descriptions present considerable detail they should be properly viewed as illustrating preferred embodiments of the present invention rather than limiting the scope of the invention. Many more embodiments following the same principles will occur to those skilled in the art. As one example, some embodiments will include only a single lateral strap instead of a pair of opposing lateral straps. Accordingly, the scope of the invention should be fixed by the following claims rather than by the examples given.

Having described my invention, I claim:

1. A method for providing a reconfigurable sling for a user having an affected arm with an upper arm, and a lower arm, and a torso, comprising:

(a) providing a belt assembly with an abduction pillow including an anterior surface, a
posterior surface, a lateral surface, a medial surface, and a superior surface;
(b) securing said belt assembly around said torso of said user with said lateral surface of said abduction pillow facing away from said user;
(c) providing a reconfigurable sling, including,
(i) a proximal panel having a superior edge,
(ii) a distal panel having a superior edge,
(iii) a central panel joining said proximal panel and said distal panel,
(iv) an upper arm loop,
(v) a superior securement flap extending medially from said proximal panel,
(vi) a superior securing tab attached to said distal panel;
(d) attaching said reconfigurable sling to said lower arm by passing said proximal panel, said central panel, and said distal panel around said lower arm and securing said superior securing tab to said superior securement flap;
(e) attaching said reconfigurable sling to said upper arm by said upper arm loop passing around said upper arm;
(f) attaching said reconfigurable sling to said abduction pillow by securing said superior securement strap to said abduction pillow; and
(g) opening said reconfigurable sling by detaching said superior securing tab, whereby said lower arm is free to move but said upper arm remains restrained by said upper arm loop.

2. The method for providing a reconfigurable sling as recited in claim 1, comprising:

(a) providing a lateral securing strap on said proximal panel; and
(b) securing said lateral securing strap on said proximal panel to said lateral surface on said abduction pillow.

3. The method for providing a reconfigurable sling as recited in claim 2, comprising:

(a) providing an anterior extension on said lateral securement strap; and (b) securing said anterior extension to said anterior surface of said abduction pillow.

4. The method for providing a reconfigurable sling as recited in claim 3, comprising:

(a) providing a posterior extension on said lateral securement strap; and (b) securing said posterior extension to said posterior surface of said abduction pillow.

5. The method for providing a reconfigurable sling as recited in claim 1, comprising after opening said reconfigurable sling and releasing said lower arm, placing said lower arm back in said reconfigurable sling and securing said lower arm within said sling by securing said superior securing tab to said superior securing flap.

6. The method for providing a reconfigurable sling as recited in claim 1, comprising:

(a) providing a securing loop on said reconfigurable sling;

(b) providing a strap, having a free end, wherein said free end is formed into said upper arm loop before passing through said securing loop;

(c) adjusting a position of said free end of said strap, thereby adjusting a size of said upper arm loop; and (d) securing said free end of said strap to said reconfigurable sling.

7. The method for providing a reconfigurable sling as recited in claim 1, comprising providing a target strip to assist said user in properly positioning said superior securing tab.

8. A method for providing a reconfigurable sling for a user having an affected arm with an upper arm, and a lower arm, and a torso, comprising:

(a) providing a belt assembly with an abduction pillow including an anterior surface, a posterior surface, a lateral surface, a medial surface, and a superior surface;

(b) securing said belt assembly around said torso of said user with said lateral surface of said abduction pillow facing away from said user;

(c) providing a reconfigurable sling, including, (i) a proximal panel, (ii) a distal panel, (iii) a central panel joining said proximal panel and said distal panel, (iv) an upper arm loop, (v) a superior securement flap extending medially from said proximal panel, (vi) a superior securing tab attached to said distal panel;

(d) attaching said reconfigurable sling to said lower arm by passing said proximal panel, said central panel, and said distal panel around said lower arm and securing said superior securing tab to said superior securement flap;

(e) attaching said reconfigurable sling to said upper arm by placing said upper arm within said upper arm loop;

(f) attaching said reconfigurable sling to said abduction pillow by securing said superior securement strap to said abduction pillow; and (g) opening said reconfigurable sling by detaching said superior securing tab, whereby said lower arm is free to move but said upper arm remains restrained by said upper arm loop.

9. The method for providing a reconfigurable sling as recited in claim 8, comprising:

(a) providing a lateral securing strap on said proximal panel; and (b) securing said lateral securing strap on said proximal panel to said lateral surface on said abduction pillow.

10. The method for providing a reconfigurable sling as recited in claim 9, comprising:

(a) providing an anterior extension on said lateral securement strap; and (b) securing said anterior extension to said anterior surface of said abduction pillow.

11. The method for providing a reconfigurable sling as recited in claim 10, comprising:

(a) providing a posterior extension on said lateral securement strap; and (b) securing said posterior extension to said posterior surface of said abduction pillow.

12. The method for providing a reconfigurable sling as recited in claim 8, comprising after opening said reconfigurable sling and releasing said lower arm, placing said lower arm back in said reconfigurable sling and securing said lower arm within said sling by securing said superior securing tab to said superior securing flap.

13. The method for providing a reconfigurable sling as recited in claim 8, comprising:

(a) providing a securing loop on said reconfigurable sling;

(b) providing a strap, having a free end, wherein said free end is formed into said upper arm loop before passing through said securing loop;

(c) adjusting a position of said free end of said strap, thereby adjusting a size of said upper arm loop; and (d) securing said free end of said strap to said reconfigurable sling.

14. The method for providing a reconfigurable sling as recited in claim 8, comprising providing a target strip to assist said user in properly positioning said superior securing tab.

15. A method for providing a reconfigurable sling for a user having an affected arm with an upper arm, and a lower arm, and a torso, comprising:

(a) providing a belt assembly with an abduction pillow including a lateral surface;

(b) securing said belt assembly around said torso of said user with said lateral surface of said abduction pillow facing away from said user;

(c) providing a reconfigurable sling, including, (i) a proximal panel, (ii) a distal panel, (iii) a central panel joining said proximal panel and said distal panel, (iv) an upper arm loop, (v) a securing tab attached to said distal panel;

(d) attaching said reconfigurable sling to said lower arm by passing said proximal panel, said central panel, and said distal panel around said lower arm and securing said securing tab;

(e) attaching said reconfigurable sling to said upper arm by placing said upper arm within said upper arm loop;

(f) attaching said reconfigurable sling to said abduction pillow; and (g) opening said reconfigurable sling by detaching said securing tab, whereby said lower arm is free to move but said upper arm remains restrained by said upper arm loop.

16. The method for providing a reconfigurable sling as recited in claim 15, comprising after opening said reconfigurable sling and releasing said lower arm, placing said lower arm back in said reconfigurable sling and securing said lower arm within said sling by securing said securing tab.

17. The method for providing a reconfigurable sling as recited in claim 15, comprising:

(a) providing a securing loop on said reconfigurable sling;

(b) providing a strap, having a free end, wherein said free end is formed into said upper arm loop before passing through said securing loop;

(c) adjusting a position of said free end of said strap, thereby adjusting a size of said upper arm loop; and (d) securing said free end of said strap to said reconfigurable sling.

18. The method for providing a reconfigurable sling as recited in claim 15, comprising providing a target strip to assist said user in properly positioning said securing tab.

19. The method for providing a reconfigurable sling as recited in claim 15, comprising:

(a) providing a lateral securing strap on said proximal panel; and (b) securing said lateral securing strap on said proximal panel to said lateral surface on said abduction pillow.

20. The method for providing a reconfigurable sling as recited in claim 15, comprising:

(a) providing an anterior extension on said lateral securement strap; and (b) securing said anterior extension to said anterior surface of said abduction pillow.

* * * * *